US009556453B2

(12) United States Patent
Meade et al.

(10) Patent No.: US 9,556,453 B2
(45) Date of Patent: *Jan. 31, 2017

(54) INSECT RESISTANCE MANAGEMENT WITH COMBINATIONS OF CRY1BE AND CRY1F PROTEINS

(75) Inventors: Thomas Meade, Zionsville, IN (US); Kenneth Narva, Zionsville, IN (US); Nicholas P. Storer, Kensington, MD (US); Joel J. Sheets, Zionsville, IN (US); Stephanie L. Burton, Indianapolis, IN (US); Aaron T. Woosley, Fishers, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 1084 days.

This patent is subject to a terminal disclaimer.

(21) Appl. No.: 13/516,629

(22) PCT Filed: Dec. 16, 2010

(86) PCT No.: PCT/US2010/060808
§ 371 (c)(1),
(2), (4) Date: Aug. 27, 2012

(87) PCT Pub. No.: WO2011/075584
PCT Pub. Date: Jun. 23, 2011

(65) Prior Publication Data
US 2012/0311746 A1     Dec. 6, 2012

Related U.S. Application Data

(60) Provisional application No. 61/284,290, filed on Dec. 16, 2009.

(51) Int. Cl.
*C12N 15/82* (2006.01)
*A01N 63/02* (2006.01)
*A01N 65/00* (2009.01)

(52) U.S. Cl.
CPC ........... *C12N 15/8286* (2013.01); *A01N 63/02* (2013.01); *A01N 65/00* (2013.01)

(58) Field of Classification Search
None
See application file for complete search history.

(56) References Cited

U.S. PATENT DOCUMENTS

| 5,723,758 | A | 3/1998 | Payne et al. | |
| 5,827,514 | A | 10/1998 | Bradfisch et al. | |
| 5,866,784 | A * | 2/1999 | Van Mellaert et al. | 800/302 |
| 6,218,188 | B1 * | 4/2001 | Cardineau et al. | 435/468 |
| 7,078,509 | B2 * | 7/2006 | Baum et al. | 536/23.1 |
| 2001/0026940 | A1 | 10/2001 | Cardineau et al. | |
| 2003/0186813 | A1 | 10/2003 | Pershing et al. | |
| 2005/0155103 | A1 | 7/2005 | Baum et al. | |
| 2006/0112447 | A1 * | 5/2006 | Bogdanova | C07K 14/325 800/279 |
| 2007/0006340 | A1 | 1/2007 | Lang et al. | |

FOREIGN PATENT DOCUMENTS

| CN | 1314911 A | 9/2001 |
| WO | WO 99/24581 A2 | 5/1999 |
| WO | WO 2005/103266 A1 | 11/2005 |
| WO | WO 2009/132850 A1 | 11/2009 |

OTHER PUBLICATIONS

Crickmore et al (2014 "Bacillus thuringiensis toxin nomenclature" http://www.btnomenclature.info/)).*
Hua et al (2001, Appl. Environ. Microbiol. 67:872-879).*
Denolf et al (1993, Appl. Environ. Microbiol. 59:1828-1837).*
Bates et al (2005, Nature Biotechnol. 23:57-62).*
van Fankenhuyzen (2009, J. Invert. Pathol. 101:1-16).*
Luo et al, 1999, Appl. Environ. Microbiol. 65:457-464.*
Gatehouse. Biotechnological Prospects for Engineering Insect-Resistant Plants. Plant Physiology, Mar. 2008, vol. 146, No. 3, p. 881-887, p. 882, para 3, para 4.
Neppl, Management of Resistance to Bacillus thuringiensis Toxins, The Environmental Studies Program—The University of Chicago, May 26, 2000 [online]. [Retrieved on Feb. 12, 2011]. Retrieved from the internet: URL:http://camillapede.tripod.com/bapaper.html p. 4, para 6; p. 5, para 3-4; p. 9, para 4.
Bravo A et al: "How to cope with insect resistance to Bt toxins?", Trends in Biotechnology, Elsevier Publication, Cambridge, GB, vol. 26, No. 10, Oct. 2, 2008 (Oct. 2, 2008), pp. 573-579, XP025406825, ISSN: 0167-7799, DOI: 10.1016/J.TIBTECH.2008.06.005 [retrieved on Feb. 14, 2008] *the whole document*.
Gutierrez, et al., Physiologically based demographics of Bt cotton-pest interactions I. Pink bollworm resistance, refuge and risk, Andrew Paul Gutierrez et al., Ecological Modelling, 2006., vol. 191, pp. 346-359, claims 16, 20, 23, 29, 32, 41-42.
Song, et al., Carboxy-terminal half of Cry1C can help vegetative insecticidal protein to form inclusion bodies in the mother cell of Bacillus thuringiensis, Applied Microbiol Biotechnol (2008) 80:647-654.

(Continued)

*Primary Examiner* — Anne Kubelik
(74) *Attorney, Agent, or Firm* — Ronald S. Maciak; Barnes & Thornburg LLP

(57) ABSTRACT

The subject invention relates in part to stacking Cry1Be toxins along with Cry1Fa toxins to prevent insects from developing resistance towards either toxin by itself. As discussed in more detail herein, the subject pair of proteins is a particularly advantageous combination, as no other pair of proteins is known to provide high levels of control and non-cross-resistant activity against both *Spodoptera frugiperda* (FAW) and *Ostrinia nubilalis* (ECB) insects. This dual, non-cross-resistant activity is also advantageous because it can reduce the number of proteins/genes needed to target these insects with multiple, non-cross-resistant proteins. This can reduce or eliminate the need for refuge acreage. Accordingly, the subject invention also relates generally to using four genes to provide three proteins for non-cross-resistant control of a first insect, and three proteins for non-cross-resistant control of a second insect. In preferred embodiments, the targeted insects are FAW and ECB.

22 Claims, 2 Drawing Sheets

(56) References Cited

OTHER PUBLICATIONS

Rang, C. et al., Competition of Bacillus Thuringiensis Cry1 Toxins for Midgut Binding Sites: A Basis for the Development and Management of Transgenic Tropical Maize Resistant to Several Stemborers, An International Journal, 2004, pp. 22-27, vol. 49, Springer-Verlag, New York.

Gonzalez-Cabrera, J. et al., Toxicity and Mode of Action of Bacillus Thuringiensis Cry Proteins in the Mediterranean Corn Borer, Sesamia Nonagrioides (Lefebvre), Applied and Environmental Microbiology, 2006, pp. 2594-2600, vol. 72, No. 4, American Society for Microbiology.

\* cited by examiner

Figure 1. Competition binding of [125I] Cry1Fa vs Cry1Fa or Cry1Be to brush border membrane vesicles produced from *Spodoptera frugiperda* (fall armyworm, FAW). Assays conducted in duplicate using pull-down method. FAW-0 represents [125I] Cry1Fa bound to receptors in the absence of any competing ligand (control). FAW-1,000 nM Cry1Fa represents the greatly reduced level of binding obtained in the presence of homologous non-labeled Cry1Fa which displaced the binding of the radiolabeled Cry1Fa from its receptor. FAW-1,000 nM Cry1Be represents the binding obtained in the presence of non-labeled Cry1Be which could not displace the binding of the radiolabeled Cry1Fa from its receptor.

Figure 2. Competition binding of [125I] Cry1Fa vs Cry1Fa or Cry1Be to brush border membrane vesicles produced from *Ostrinia nubilalis* (European corn borer, ECB). Assays conducted in duplicate using pull-down method. Control Rxn. represents [125I] Cry1Fa bound to receptors in the absence of any competing ligand. 1,000 nM Cry1Fa represents the greatly reduced level of binding obtained in the presence of homologous non-labeled Cry1Fa which displaced the binding of the radiolabeled Cry1Fa from its receptor. 1,000 nM Cry1Be represents the binding obtained in the presence of non-labeled Cry1Be which could not displace the binding of the radiolabeled Cry1Fa from its receptor.

Figure 3. Competitive displacement of $^{125}$I Cry1Be binding to brush border membrane vesicles produced from *Spodoptera frugiperda* by Cry1Fa (▲) and Cry1Be (●). Cry1Fa effectively displaces the binding of 0.5 nM $^{125}$I Cry1Be only at concentrations greater than 100 nM (200-times the concentration of radiolabeled Cry1Be used in the assay). Cry1Be is much more effective at displacing itself as compared to Cry1Fa, even though Cry1Fa is more active against this pest than Cry1Be.

1

INSECT RESISTANCE MANAGEMENT WITH COMBINATIONS OF CRY1BE AND CRY1F PROTEINS

CROSS-REFERENCE TO RELATED APPLICATIONS

This is a national phase application, filed pursuant to 35 U.S.C. §371, of PCT application No. PCT/US10/60808 filed on Dec. 16, 2010, which claims the benefit of U.S. provisional application No. 61/284,290, filed on Dec. 16, 2009. The prior applications are incorporated herein by reference in their entirety.

BACKGROUND

Humans grow corn for food and energy applications. Insects eat and damage corn plants and thereby undermine these human efforts.

Current in-plant transgenic control of these pests is achieved through plant expression of a crystal (Cry) delta endotoxin gene coding for the Cry1Fa protein from *Bacillus thuringiensis*. Cry1Fa is the protein toxin currently in the Herculex™ brand of Dow AgroSciences transgenic corn seeds (Herculex, Herculex-Extra, and Herculex-RW) that are resistant to fall armyworm (FAW, *Spodoptera frugiperda*) and European corn borer (ECB, *Ostrinia nubilalis*) insect pests. This protein works by binding to specific receptor(s) located in the midgut of insects, and forms pores within the gut cells. The formation of these pores prevents insects from regulating osmotic balance which results in their death.

However, some are concerned that insects might be able to develop resistance to the action of Cry1Fa through genetic alterations of the receptors within their gut that bind Cry1Fa. Insects that produce receptors with a reduced ability to bind Cry1Fa can be resistant to the activity of Cry1Fa, and thus survive on plants that express this protein.

With a single Cry toxin continuously present in the plant during growth conditions, there is concern that insects could develop resistance to the activity of this protein through genetic alterations of the receptor that binds Cry1Fa toxin in the insect gut. Reductions in toxin binding due to these alterations in the receptor would lead to reduced toxicity of the Cry1Fa possibly leading to eventual decreased effectiveness of the protein when expressed in a crop. See e.g. US 2009 0313717, which relates to a Cry2 protein plus a Vip3Aa, Cry1F, or Cry1A for control of *Helicoverpa zea* or *armigera*. WO 2009 132850 relates to Cry1F or Cry1A and Vip3Aa for controlling *Spodoptera frugiperda*. US 2008 0311096 relates to Cry1Ab for controlling Cry1F-resistant ECB.

Additional Cry toxins are listed at the website of the official B.t. nomenclature committee (Crickmore et al.; lifesci.sussex.ac.uk/home/Neil_Crickmore/Bt/). See Appendix A, attached. There are currently nearly 60 main groups of "Cry" toxins (Cry1-Cry59), with additional Cyt toxins and VIP toxins and the like. Many of each numeric group have capital-letter subgroups, and the capital letter subgroups have lower-cased letter sub-subgroups. (Cry1 has A-L, and Cry1A has a-i, for example).

The van Frankenhuyzen (2009) reference (*J. Invert. Pathol.* 101:1-16), for example, illustrates that there are many target pests and a great number of toxins that could potentially be selected to control the target pests. See e.g. FIG. 3 of van Frankenhuyzen. One (among many) pests that could be targeted would include *Ostrinia nubilalis*, and for this insect, FIG. 3 of van Frankenhuyzen shows 17 toxins that are active against ECB, and one that is possibly active. This is not an exhaustive list of the options.

FIG. 3 of van Frankenhuyzen also illustrates that each Cry protein has a unique spectrum of activity—they are active against some insects but not others. Cry proteins typically bind receptors on cells in the insect gut, and this is one factor that influences the spectrum of activity. Receptors for one Cry protein can be found in some insects but not in others; a given insect might have receptors for one or more Cry proteins but not for other Cry proteins.

Given many possible insects to target, and many possible Cry proteins that could be active against any given insect, numbers alone illustrate the complexity of the problem of resistance management. Considering just the 18 proteins identified by van Frankenhuyzen as active or possibly against ECB, this would allow for hundreds of possible pairs of toxins to test in combination.

In addition, assaying for competitive/non-competitive binding is no easy task. It can involve radio-active labeling and assaying for displacement of radioactively labeled proteins. This in and of itself can be a complex art.

Attempting to use resistant insects, directly, is also complicated. Resistant strains of insects would have to be developed against a given protein. Siqueira (June 2004; *J. Econ. Entomol.*, 97(3):1049-1057) states (in the abstract) that " . . . tests for cross-resistance among different toxins have been limited by a lack of resistant colonies." This illustrates difficulties with obtaining resistant insect strains for assaying proteins for resistance management potential. When pairs of proteins are involved, either protein could be used in an attempt to screen for the development of resistant insects.

Siqueira also states, in the abstract, that selection with Cry1Ab (i.e., developing colonies of ECB that are resistant to Cry1Ab) " . . . resulted in decreased susceptibility to a number of other toxins . . . . " This illustrates the phenomenon of cross-resistance. Cry1Ab-resistant ECB were cross-resistant to "a number of other toxins."

Thus, selecting two proteins that are active against the same (non-resistant) insect is a mere starting point of the analysis, if resistance issues are to be addressed. Activity levels against non-resistant insects is another factor. FIG. 11 of van Frankenhuyzen shows that even among a group of 12 toxins selected for testing against ECB (non-resistant), other Cry proteins (such as Cry1Ac, Cry1Bb, and Cry2Aa) could be more active than the ones now claimed for controlling ECB.

BRIEF SUMMARY

The subject invention relates in part to stacking Cry1Be proteins along with Cry1Fa proteins resulting in products that are more durable and less prone towards insects developing resistance towards either protein by itself.

As discussed in more detail herein, the subject pair of proteins is a particularly advantageous combination, as no other pair of proteins is known to provide high levels of control and non-cross-resistant action against both *Spodoptera frugiperda* (FAW) and *Ostrinia nubilalis* (ECB) insects.

This dual, non-cross-resistant activity is also advantageous because it can reduce the number of proteins/genes needed to target these insects with multiple, non-cross-resistant proteins. This can reduce or eliminate the need for refuge acreage. Accordingly, the subject invention also relates generally to using four genes to provide three proteins for non-cross-resistant control of FAW and three proteins for non-cross-resistant control of ECB.

DETAILED DESCRIPTION

The subject invention includes the use of Cry1Be proteins with Cry1Fa proteins as a pair. The subject invention also relates in part to triple stacks or "pyramids" of three (or more) toxins, with Cry1Fa and Cry1Be proteins being the base pair. The subject base pair of proteins provides two proteins providing non-cross-resistant action against two insects—the fall armyworm (FAW; *Spodoptera frugiperda*) and the European cornborer (ECB; *Ostrinia nubilalis*). This makes the subject pair of proteins a particularly advantageous combination, as no other pair of proteins is known to provide high levels of control and non-cross-resistant action against these two insects.

In some preferred pyramid embodiments, another protein can be added to the subject base pair to provide a third protein having action against ECB. Some of these preferred pyramid combinations are a Cry1Fa protein plus a Cry1Be protein plus another toxin/gene selected from the group consisting of Cry1Ab, Cry2Aa, Cry1I, and DIG-3 proteins.

In some preferred pyramid embodiments, another protein can be added to the subject base pair to provide a third protein having action against FAW. Some of these preferred pyramid combinations are Cry1Fa plus Cry1Be plus another toxin/gene selected from the group consisting of Vip3A, Cry1C, Cry1D, and Cry1E.

In some preferred embodiments, and in light of the activity of both Cry1F and Cry1Be against both ECB and FAW, the subject invention allows for the use of four proteins wherein three of the four proteins provide non-cross-resistant action against ECB, and three of the four proteins provide non-competitive action against FAW). Preferred quad stacks are Cry1Fa plus Cry1Be plus: Cry1C, Cry1D, Cry1E, or Vip3 (for targeting FAW), plus Cry1Ab, Cry2A, Cry1I, or DIG-3 (for targetting ECB).

Concurrently filed application entitled "Use of Vip3Ab for management of resistant insects" provides data showing that Vip3Ab is useful with Cry1F for managing insecticidal protein resistance in FAW, and that Vip3Ab and Cry1F do not competitively bind to FAW membrane preparations.

U.S. Ser. No. 61/284,281 (filed Dec. 16, 2009) shows that Cry1C is active against Cry1F-resistant FAW, and U.S. Ser. No. 61/284,252 (filed Dec. 16, 2009) shows that Cry1D is active against Cry1F-resistant FAW. These two applications also show that Cry1C does not compete with Cry1F for binding in FAW membrane preparations, and that Cry1D does not compete with Cry1F for binding in FAW membrane preparations.

U.S. Ser. No. 61/284,278 (filed Dec. 16, 2009) shows that Cry2A is active against Cry1F-resistant ECB.

Cry1Ab is disclosed in US 2008 0311096 as being useful for controlling Cry1F-resistant ECBs.

DIG-3 is disclosed in US 2010 0269223.

Vip3 toxins, for example, (including Vip3Ab in some preferred embodiments) are listed in the attached Appendix A. Cry proteins are also listed. Those GENBANK numbers can also be used to obtain the sequences for any of the genes and proteins disclosed or mentioned herein.

The subject invention also relates generally to the use of three insecticidal proteins (Cry proteins in some preferred embodiments) that do not cause cross-resistance with each other against a single target pest. The subject invention also relates generally to the use of four insecticidal proteins (Cry and Vip proteins in some preferred embodiments) that, in combination, provide high levels of control and non-cross-resistant activity against two target insects Plants (and acreage planted with such plants) that produce combinations of the subject proteins are included within the scope of the subject invention. Additional toxins/genes can also be added, but preferred triple and quad (four-protein/gene) stacks would, according to the subject invention, advantageously and surprisingly provide three proteins with non-competitive action against FAW and/or ECB. This can help to reduce or eliminate the requirement for refuge acreage (e.g., less than 40%, less than 20%, less than 10%, less than 5%, or even 0% refuge). A field thus planted of over 10 acres is thus included within the subject invention.

The subject polynucleotide(s) are preferably in a genetic construct under control (operably linked/comprising) of a non-*Bacillus-thuringiensis* promoter. The subject polynucleotides can comprise codon usage for enhanced expression in a plant.

To counter act the ability of insects to develop resistance to Cry1Fa, we identified Cry toxins that non-competitively (with Cry1Fa) bind to protein receptors. Cry1Fa does not to displace Cry1Be binding to receptors located in the insect gut of FAW and ECB larvae. We found that Cry1Be Cry proteins that either interact with completely different receptors, or only partially overlap in their receptor interactions compared to Cry1Fa. The ability of these Cry1Be toxins to be toxic to FAW and ECB larvae, yet not fully interact with the same receptor sites as Cry1Fa, shows that their toxicity will not be affected by insects having developed genetic alterations of their Cry1Fa receptor as a mechanism to become resistant to the toxicity of Cry1Fa. Thus insects having developed resistance to Cry1Fa through a reduction in the ability of its gut receptors to bind Cry1Fa would still be susceptible to the toxicity of Cry1Be proteins which bind alternative receptor sites. We obtained biochemical data that supports this.

Having combinations of these proteins expressed in transgenic plants will thus be a useful and valuable mechanism to reduce the probability for the development of insect resistance in the field and thus lead towards a reduction in the requirement for refuge. These Cry1Be proteins have been studied for their activity against other major insect pests, both sensitive, and those resistant to Cry1Fa (rFAW and rECB), as shown in Table 1, Cry1Be is active against both resistant and susceptible ECB larvae. These data show the Cry1Be toxin interacting at separate target site(s) within the insect gut compared to Cry1Fa—thus making excellent stacking partners.

Stacking Cry1Fa expressing crops with one or more additional Cry genes, such as those expressing a Cry1Be protein toxins would result in an effective management strategy to prevent the ability of insects to develop tolerance to the activity of transgenic plants expressing these protein toxins. Since we show that the Cry1Be proteins interact at different sites compared to Cry1Fa, if resistance were to occur through alterations in the affinity of the insect gut receptors that bind to the Cry toxins, the alteration would have to occur in at least two different receptors simultaneously to allow the insects to survive on plants expressing the multiple proteins. The probability of this occurring is extremely remote, thus increasing the durability of the transgenic product to ward of insects being able to develop tolerance to the proteins.

We radio-iodinated trypsin truncated forms of Cry1Be protein toxins and used radioreceptor binding assay techniques to measure their binding interaction with putative receptor proteins located within the insect gut membranes.

The gut membranes were prepared as brush border membrane vesicles (BBMV) by the method of Wolfersberger. Iodination of the toxins were conducted using either iodo beads or iodogen treated tubes from Pierce Chemicals. Specific activity of the radiolabeled toxin was approximately 1-4 µCi/µg protein. Binding studies were carried out essentially by the procedures of Liang.

Additional competitive binding data using labeled Cry1Fa is also presented below in the Examples section. These data also show non-cross-resistant activity of Cry1Fa and Cry1Be against both ECB and FAW.

The data presented herein shows that Cry1Be proteins interact at separate target site within the insect gut compared to Cry1Fa. Thus, these two proteins make excellent stacking partners.

Genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

As used therein, the boundaries represent approximately 95% (Cry1Fa's and 1Be's), 78% (Cry1F's and Cry1B's), and 45% (Cry1's) sequence identity, per "Revision of the Nomenclature for the *Bacillus thuringiensis* Pesticidal Crystal Proteins," N. Crickmore, D. R. Zeigler, J. Feitelson, E. Schnepf, J. Van Rie, D. Lereclus, J. Baum, and D. H. Dean. Microbiology and Molecular Biology Reviews (1998) Vol 62: 807-813. These cut offs can also be applied to the core proteins only (for Cry1Fa and Cry1Be core proteins, for example).

Fragments and equivalents that retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments of genes encoding proteins that retain pesticidal activity are also included in this definition.

A further method for identifying the genes encoding the toxins and gene portions useful according to the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) DNA Probes, Stockton Press, New York, N.Y., pp. 169-170. Some examples of salt concentrations and temperature combinations are as follows (in order of increasing stringency): 2×SSPE or SSC at room temperature; 1×SSPE or SSC at 42° C.; 0.1×SSPE or SSC at 42° C.; 0.1×SSPE or SSC at 65° C. Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Certain proteins of the subject invention have been specifically exemplified herein. Since these proteins are merely exemplary of the proteins of the subject invention, it should be readily apparent that the subject invention comprises variant or equivalent proteins (and nucleotide sequences coding for equivalent proteins) having the same or similar pesticidal activity of the exemplified protein. Equivalent proteins will have amino acid homology with an exemplified protein. This amino acid homology will typically be greater than 75%, preferably be greater than 90%, and most preferably be greater than 95%. The amino acid homology will be highest in critical regions of the protein which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Following is a listing of examples of amino acids belonging to each class. In some instances, non-conservative substitutions can also be made. The critical factor is that these substitutions must not significantly detract from the biological activity of the protein.

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Plant Transformation.

A preferred recombinant host for production of the insecticidal proteins of the subject invention is a transformed plant. Genes encoding Bt toxin proteins, as disclosed herein, can be inserted into plant cells using a variety of techniques which are well known in the art. For example, a large number of cloning vectors comprising a replication system in *Escherichia coli* and a marker that permits selection of the transformed cells are available for preparation for the insertion of foreign genes into higher plants. The vectors comprise, for example, pBR322, pUC series, M13 mp series, pACYC184, inter alia. Accordingly, the DNA fragment having the sequence encoding the Bt toxin protein can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and sufficiently described in EP 120 516, Lee and Gelvin (2008), Hoekema (1985), Fraley et al., (1986), and An et al., (1985), and is well established in the art.

Once the inserted DNA has been integrated in the plant genome, it is relatively stable. The transformation vector normally contains a selectable marker that confers on the transformed plant cells resistance to a biocide or an antibiotic, such as Bialaphos, Kanamycin, G418, Bleomycin, or Hygromycin, inter alia. The individually employed marker should accordingly permit the selection of transformed cells rather than cells that do not contain the inserted DNA.

A large number of techniques is available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If *Agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation). Binary vectors can replicate themselves both in *E. coli* and in *Agrobacteria*. They comprise a selection marker gene and a linker or polylinker which are framed by the Right and Left T-DNA border regions. They can be transformed directly into *Agrobacteria* (Holsters et al., 1978). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831, which is hereby incorporated by reference. While some truncated toxins are exemplified herein, it is well-known in the Bt art that 130 kDa-type (full-length) toxins have an N-terminal half that is the core toxin, and a C-terminal half that is the protoxin "tail." Thus, appropriate "tails" can be used with truncated/core toxins of the subject invention. See e.g. U.S. Pat. No. 6,218,188 and U.S. Pat. No. 6,673,990. In addition, methods for creating synthetic Bt genes for use in plants are known in the art (Stewart and Burgin, 2007). One non-limiting example of a preferred transformed plant is a fertile maize plant comprising a plant expressible gene encoding a Cry1Fa protein, and further comprising a second plant expressible gene encoding a Cry1Ca protein.

Transfer (or introgression) of the Cry1Fa- and Cry1Ca-determined trait(s) into inbred maize lines can be achieved by recurrent selection breeding, for example by backcrossing. In this case, a desired recurrent parent is first crossed to a donor inbred (the non-recurrent parent) that carries the appropriate gene(s) for the Cry1F- and Cry1C-determined traits. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376).

Insect Resistance Management (IRM) Strategies.

Roush et al., for example, outlines two-toxin strategies, also called "pyramiding" or "stacking," for management of insecticidal transgenic crops. (The Royal Society. *Phil. Trans. R. Soc. Lond. B.* (1998) 353, 1777-1786).

On their website, the United States Environmental Protection Agency (epa.gov/oppbppd1/biopesticides/pips/bt_corn_refuge_2006.htm) publishes the following requirements for providing non-transgenic (i.e., non-B.t.) refuges (a section or block of non-Bt crops/corn) for use with transgenic crops producing a single Bt protein active against target pests.

"The specific structured requirements for corn borer-protected Bt (Cry1Ab or Cry1F) corn products are as follows:
Structured refuges:
   20% non-Lepidopteran Bt corn refuge in Corn Belt;
   50% non-Lepidopteran Bt refuge in Cotton Belt
Blocks
   Internal (i.e., within the Bt field)
   External (i.e., separate fields within ½ mile (¼ mile if possible) of the Bt field to maximize random mating)
In-field Strips
   Strips must be at least 4 rows wide (preferably 6 rows) to reduce the effects of larval movement"

In addition, the National Corn Growers Association, on their website: (ncga.com/insect-resistance-management-fact-sheet-bt-corn) also provides similar guidance regarding the refuge requirements. For example:

"Requirements of the Corn Borer IRM:
Plant at least 20% of your corn acres to refuge hybrids
In cotton producing regions, refuge must be 50%
Must be planted within ½ mile of the refuge hybrids
Refuge can be planted as strips within the Bt field; the refuge strips must be at least 4 rows wide
Refuge may be treated with conventional pesticides only if economic thresholds are reached for target insect
Bt-based sprayable insecticides cannot be used on the refuge corn
Appropriate refuge must be planted on every farm with Bt corn"

As stated by Roush et al. (on pages 1780 and 1784 right column, for example), stacking or pyramiding of two different proteins each effective against the target pests and with little or no cross-resistance can allow for use of a smaller refuge. Roush suggests that for a successful stack, a refuge size of less than 10% refuge, can provide comparable resistance management to about 50% refuge for a single (non-pyramided) trait. For currently available pyramided Bt corn products, the U.S. Environmental Protection Agency requires significantly less (generally 5%) structured refuge of non-Bt corn be planted than for single trait products (generally 20%).

There are various ways of providing the IRM effects of a refuge, including various geometric planting patterns in the fields (as mentioned above) and in-bag seed mixtures, as discussed further by Roush et al. (supra), and U.S. Pat. No. 6,551,962.

The above percentages, or similar refuge ratios, can be used for the subject double or triple stacks or pyramids. For triple stacks with three modes of action against a single target pest, a goal would be zero refuge (or less than 5% refuge, for example). This is particularly true for commercial acreage—of over 10 acres for example.

All patents, patent applications, provisional applications, and publications referred to or cited herein are incorporated by reference in their entirety to the extent they are not inconsistent with the explicit teachings of this specification. Unless specifically indicated or implied, the terms "a", "an", and "the" signify "at least one" as used herein.

REFERENCES

Wolfersberger, M. G., (1993), Preparation and Partial Characterization of Amino Acid Transporting Brush Border Membrane Vesicles from the Larval Midgut of the Gypsy Moth (*Lymantria Dispar*). Arch. Insect Biochem. Physiol. 24: 139-147.

Liang, Y., Patel, S. S., and Dean, D. H., (1995), Irreversible Binding Kinetics of *Bacillus thuringiensis* Cry1A Delta-Endotoxins to Gypsy Moth Brush Border Membrane Vesicles is Directly Correlated to Toxicity. J. Biol. Chem., 270, 24719-24724.

EXAMPLES

Example 1

Bioactivity

Bioassay results of the subject Cry proteins acting on FAW, ECB, and Cry1Fa resistant FAW and ECB insects are shown in Table 1. Both proteins are highly active against FAW larvae. (For a discussion of this pest, see e.g. Tabashnik, *PNAS* (2008), vol. 105 no. 49, 19029-19030.) Cry1Fa is much less active against FAW that are resistant towards the toxicity of Cry1Fa (rFAW) as compare to sensitive FAW. Cry1Be is as active, or more active, against rFAW as compared to sensitive FAW.

TABLE 1

Table 1. Biological activity of Cry proteins against four different insect types, plus Cry1Fa resistant FAW and ECB larvae. Non-underlined values in green are LC-50 values expressed as ranges of values obtained from multiple determinations. Underlined values are GI-50 values where the protein does not result in lethality against the particular insect. Values are in ng/cm².

| PROTEIN | CEW | FAW | rFAW | ECB | rECB | BCW |
|---|---|---|---|---|---|---|
| Cry1Be | 400-1,000 | 1,000-2,000 | 300 | 600 | 200-1,200 | 2,000 |
| Cry1Fa | 40-120 | 20-80 | inactive | 20-100 | inactive | 200 |

Example 2

Binding Studies

FIG. 1 shows competition binding of $^{125}$I Cry1Fa versus Cry1Fa or Cry1Be to brush border membrane vesicles produced from *Spodoptera frugiperda* (fall armyworm, FAW). Assays were conducted in duplicate using the pulldown method. FAW-0 represents $^{125}$I Cry1Fa bound to receptors in the absence of any competing ligand (control). FAW-1,000 nM Cry1Fa represents the greatly reduced level of binding obtained in the presence of homologous non-labeled Cry1Fa which displaced the binding of the radiolabeled Cry1Fa from its receptor. FAW-1,000 nM Cry1Be represents the binding obtained in the presence of non-labeled Cry1Be which could not displace the binding of the radiolabeled Cry1Fa from its receptor.

FIG. 2 shows competition binding of $^{125}$I Cry1Fa versus Cry1Fa or Cry1Be to brush border membrane vesicles produced from *Ostrinia nubilalis* (European corn borer, ECB). Assays were conducted in duplicate using the pulldown method. "Control Rxn" represents $^{125}$I Cry1Fa bound to receptors in the absence of any competing ligand. 1,000 nM Cry1Fa represents the greatly reduced level of binding obtained in the presence of homologous non-labeled Cry1Fa which displaced the binding of the radiolabeled Cry1Fa from its receptor. 1,000 nM Cry1Be represents the binding obtained in the presence of non-labeled Cry1Be which could not displace the binding of the radiolabeled Cry1Fa from its receptor.

FIG. 3 shows competitive displacement of $^{125}$I Cry1Be binding to brush border membrane vesicles produced from *Spodoptera frugiperda* by Cry1Fa (▲) and Cry1Be (●). Cry1Fa effectively displaces the binding of 0.5 nM $^{125}$I Cry1Be only at concentrations greater than 100 nM (200-times the concentration of radiolabeled Cry1Be used in the assay). Cry1Be is much more effective at displacing itself as compared to Cry1Fa, even though Cry1Fa is more active against this pest than Cry1Be.

APPENDIX A

List of delta-endotoxins—from Crickmore et al. website (cited in application)
Accession Number is to NCBI entry (if available)

| Name | Acc No. | Authors | Year | Source Strain | Comment |
|---|---|---|---|---|---|
| Cry1Aa1 | AAA22353 | Schnepf et al | 1985 | Bt kurstaki HD1 | |
| Cry1Aa2 | AAA22552 | Shibano et al | 1985 | Bt sotto | |
| Cry1Aa3 | BAA00257 | Shimizu et al | 1988 | Bt aizawai IPL7 | |
| Cry1Aa4 | CAA31886 | Masson et al | 1989 | Bt entomocidus | |
| Cry1Aa5 | BAA04468 | Udayasuriyan et al | 1994 | Bt Fu-2-7 | |
| Cry1Aa6 | AAA86265 | Masson et al | 1994 | Bt kurstaki NRD-12 | |
| Cry1Aa7 | AAD46139 | Osman et al | 1999 | Bt C12 | |
| Cry1Aa8 | I26149 | Liu | 1996 | | DNA sequence only |
| Cry1Aa9 | BAA77213 | Nagamatsu et al | 1999 | Bt dendrolimus T84A1 | |
| Cry1Aa10 | AAD55382 | Hou and Chen | 1999 | Bt kurstaki HD-1-02 | |
| Cry1Aa11 | CAA70856 | Tounsi et al | 1999 | Bt kurstaki | |
| Cry1Aa12 | AAP80146 | Yao et al | 2001 | Bt Ly30 | |
| Cry1Aa13 | AAM44305 | Zhong et al | 2002 | Bt sotto | |
| Cry1Aa14 | AAP40639 | Ren et al | 2002 | unpublished | |
| Cry1Aa15 | AAY66993 | Sauka et al | 2005 | Bt INTA Mol-12 | |
| Cry1Ab1 | AAA22330 | Wabiko et al | 1986 | Bt berliner 1715 | |
| Cry1Ab2 | AAA22613 | Thorne et al | 1986 | Bt kurstaki | |
| Cry1Ab3 | AAA22561 | Geiser et al | 1986 | Bt kurstaki HD1 | |
| Cry1Ab4 | BAA00071 | Kondo et al | 1987 | Bt kurstaki HD1 | |
| Cry1Ab5 | CAA28405 | Hofte et al | 1986 | Bt berliner 1715 | |
| Cry1Ab6 | AAA22420 | Hefford et al | 1987 | Bt kurstaki NRD-12 | |
| Cry1Ab7 | CAA31620 | Haider & Ellar | 1988 | Bt aizawai IC1 | |
| Cry1Ab8 | AAA22551 | Oeda et al | 1987 | Bt aizawai IPL7 | |
| Cry1Ab9 | CAA38701 | Chak & Jen | 1993 | Bt aizawai HD133 | |
| Cry1Ab10 | A29125 | Fischhoff et al | 1987 | Bt kurstaki HD1 | |
| Cry1Ab11 | I12419 | Ely & Tippett | 1995 | Bt A20 | DNA sequence only |
| Cry1Ab12 | AAC64003 | Silva-Werneck et al | 1998 | Bt kurstaki S93 | |
| Cry1Ab13 | AAN76494 | Tan et al | 2002 | Bt c005 | |
| Cry1Ab14 | AAG16877 | Meza-Basso & Theoduloz | 2000 | Native Chilean Bt | |
| Cry1Ab15 | AAO13302 | Li et al | 2001 | Bt B-Hm-16 | |
| Cry1Ab16 | AAK55546 | Yu et al | 2002 | Bt AC-11 | |
| Cry1Ab17 | AAT46415 | Huang et al | 2004 | Bt WB9 | |
| Cry1Ab18 | AAQ88259 | Stobdan et al | 2004 | Bt | |
| Cry1Ab19 | AAW31761 | Zhong et al | 2005 | Bt X-2 | |
| Cry1Ab20 | ABB72460 | Liu et al | 2006 | BtC008 | |
| Cry1Ab21 | ABS18384 | Swiecicka et al | 2007 | Bt IS5056 | |
| Cry1Ab22 | ABW87320 | Wu and Feng | 2008 | BtS2491Ab | |
| Cry1Ab-like | AAK14336 | Nagarathinam et al | 2001 | Bt kunthala RX24 | uncertain sequence |
| Cry1Ab-like | AAK14337 | Nagarathinam et al | 2001 | Bt kunthala RX28 | uncertain sequence |
| Cry1Ab-like | AAK14338 | Nagarathinam et al | 2001 | Bt kunthala RX27 | uncertain sequence |
| Cry1Ab-like | ABG88858 | Lin et al | 2006 | Bt ly4a3 | insufficient sequence |
| Cry1Ac1 | AAA22331 | Adang et al | 1985 | Bt kurstaki HD73 | |
| Cry1Ac2 | AAA22338 | Von Tersch et al | 1991 | Bt kenyae | |
| Cry1Ac3 | CAA38098 | Dardenne et al | 1990 | Bt BTS89A | |
| Cry1Ac4 | AAA73077 | Feitelson | 1991 | Bt kurstaki PS85A1 | |
| Cry1Ac5 | AAA22339 | Feitelson | 1992 | Bt kurstaki PS81GG | |
| Cry1Ac6 | AAA86266 | Masson et al | 1994 | Bt kurstaki NRD-12 | |
| Cry1Ac7 | AAB46989 | Herrera et al | 1994 | Bt kurstaki HD73 | |
| Cry1Ac8 | AAC44841 | Omolo et al | 1997 | Bt kurstaki HD73 | |
| Cry1Ac9 | AAB49768 | Gleave et al | 1992 | Bt DSIR732 | |
| Cry1Ac10 | CAA05505 | Sun | 1997 | Bt kurstaki YBT-1520 | |
| Cry1Ac11 | CAA10270 | Makhdoom & Riazuddin | 1998 | | |
| Cry1Ac12 | I12418 | Ely & Tippett | 1995 | Bt A20 | DNA sequence only |
| Cry1Ac13 | AAD38701 | Qiao et al | 1999 | Bt kurstaki HD1 | |
| Cry1Ac14 | AAQ06607 | Yao et al | 2002 | Bt Ly30 | |
| Cry1Ac15 | AAN07788 | Tzeng et al | 2001 | Bt from Taiwan | |
| Cry1Ac16 | AAU87037 | Zhao et al | 2005 | Bt H3 | |
| Cry1Ac17 | AAX18704 | Hire et al | 2005 | Bt kenyae HD549 | |
| Cry1Ac18 | AAY88347 | Kaur & Allam | 2005 | Bt SK-729 | |
| Cry1Ac19 | ABD37053 | Gao et al | 2005 | Bt C-33 | |
| Cry1Ac20 | ABB89046 | Tan et al | 2005 | | |
| Cry1Ac21 | AAY66992 | Sauka et al | 2005 | INTA Mol-12 | |
| Cry1Ac22 | ABZ01836 | Zhang & Fang | 2008 | Bt W015-1 | |
| Cry1Ac23 | CAQ30431 | Kashyap et al | 2008 | Bt | |
| Cry1Ac24 | ABL01535 | Arango et al | 2008 | Bt 146-158-01 | |
| Cry1Ac25 | FJ513324 | Guan Peng et al | 2008 | Bt Tm37-6 | No NCBI link July 2009 |
| Cry1Ac26 | FJ617446 | Guan Peng et al | 2009 | Bt Tm41-4 | No NCBI link July 2009 |
| Cry1Ac27 | FJ617447 | Guan Peng et al | 2009 | Bt Tm44-1B | No NCBI link July 2009 |
| Cry1Ac28 | ACM90319 | Li et al | 2009 | Bt Q-12 | |
| Cry1Ad1 | AAA22340 | Feitelson | 1993 | Bt aizawai PS81I | |
| Cry1Ad2 | CAA01880 | Anonymous | 1995 | Bt PS81RR1 | |
| Cry1Ae1 | AAA22410 | Lee & Aronson | 1991 | Bt alesti | |
| Cry1Af1 | AAB82749 | Kang et al | 1997 | Bt NT0423 | |
| Cry1Ag1 | AAD46137 | Mustafa | 1999 | | |
| Cry1Ah1 | AAQ14326 | Tan et al | 2000 | | |

APPENDIX A-continued

List of delta-endotoxins—from Crickmore et al. website (cited in application)
Accession Number is to NCBI entry (if available)

| | | | | | |
|---|---|---|---|---|---|
| Cry1Ah2 | ABB76664 | Qi et al | 2005 | Bt alesti | |
| Cry1Ai1 | AAO39719 | Wang et al | 2002 | | |
| Cry1A-like | AAK14339 | Nagarathinam et al | 2001 | Bt kunthala nags3 | uncertain sequence |
| Cry1Ba1 | CAA29898 | Brizzard & Whiteley | 1988 | Bt thuringiensis HD2 | |
| Cry1Ba2 | CAA65003 | Soetaert | 1996 | Bt entomocidus HD110 | |
| Cry1Ba3 | AAK63251 | Zhang et al | 2001 | | |
| Cry1Ba4 | AAK51084 | Nathan et al | 2001 | Bt entomocidus HD9 | |
| Cry1Ba5 | ABO20894 | Song et al | 2007 | Bt sfw-12 | |
| Cry1Ba6 | ABL60921 | Martins et al | 2006 | Bt S601 | |
| Cry1Bb1 | AAA22344 | Donovan et al | 1994 | Bt EG5847 | |
| Cry1Bc1 | CAA86568 | Bishop et al | 1994 | Bt morrisoni | |
| Cry1Bd1 | AAD10292 | Kuo et al | 2000 | Bt wuhanensis HD525 | |
| Cry1Bd2 | AAM93496 | Isakova et al | 2002 | Bt 834 | |
| Cry1Be1 | AAC32850 | Payne et al | 1998 | Bt PS158C2 | |
| Cry1Be2 | AAQ52387 | Baum et al | 2003 | | |
| Cry1Be3 | FJ716102 | Xiaodong Sun et al | 2009 | Bt | No NCBI link July 2009 |
| Cry1Bf1 | CAC50778 | Arnaut et al | 2001 | | |
| Cry1Bf2 | AAQ52380 | Baum et al | 2003 | | |
| Cry1Bg1 | AAO39720 | Wang et al | 2002 | | |
| Cry1Ca1 | CAA30396 | Honee et al | 1988 | Bt entomocidus 60.5 | |
| Cry1Ca2 | CAA31951 | Sanchis et al | 1989 | Bt aizawai 7.29 | |
| Cry1Ca3 | AAA22343 | Feitelson | 1993 | Bt aizawai PS81I | |
| Cry1Ca4 | CAA01886 | Van Mellaert et al | 1990 | Bt entomocidus HD110 | |
| Cry1Ca5 | CAA65457 | Strizhov | 1996 | Bt aizawai 7.29 | |
| Cry1Ca6 | AAF37224 | Yu et al | 2000 | Bt AF-2 | |
| Cry1Ca7 | AAG50438 | Aixing et al | 2000 | Bt J8 | |
| Cry1Ca8 | AAM00264 | Chen et al | 2001 | Bt c002 | |
| Cry1Ca9 | AAL79362 | Kao et al | 2003 | Bt G10-01A | |
| Cry1Ca10 | AAN16462 | Lin et al | 2003 | Bt E05-20a | |
| Cry1Ca11 | AAX53094 | Cai et al | 2005 | Bt C-33 | |
| Cry1Cb1 | M97880 | Kalman et al | 1993 | Bt galleriae HD29 | DNA sequence only |
| Cry1Cb2 | AAG35409 | Song et al | 2000 | Bt c001 | |
| Cry1Cb3 | ACD50894 | Huang et al | 2008 | Bt 087 | |
| Cry1Cb-like | AAX63901 | Thammasittirong et al | 2005 | Bt TA476-1 | insufficient sequence |
| Cry1Da1 | CAA38099 | Hofte et al | 1990 | Bt aizawai HD68 | |
| Cry1Da2 | I76415 | Payne & Sick | 1997 | | DNA sequence only |
| Cry1Db1 | CAA80234 | Lambert | 1993 | Bt BTS00349A | |
| Cry1Db2 | AAK48937 | Li et al | 2001 | Bt B-Pr-88 | |
| Cry1Dc1 | ABK35074 | Lertwiriyawong et al | 2006 | Bt JC291 | |
| Cry1Ea1 | CAA37933 | Visser et al | 1990 | Bt kenyae 4F1 | |
| Cry1Ea2 | CAA39609 | Bosse et al | 1990 | Bt kenyae | |
| Cry1Ea3 | AAA22345 | Feitelson | 1991 | Bt kenyae PS81F | |
| Cry1Ea4 | AAD04732 | Barboza-Corona et al | 1998 | Bt kenyae LBIT-147 | |
| Cry1Ea5 | A15535 | Botterman et al | 1994 | | DNA sequence only |
| Cry1Ea6 | AAL50330 | Sun et al | 1999 | Bt YBT-032 | |
| Cry1Ea7 | AAW72936 | Huehne et al | 2005 | Bt JC190 | |
| Cry1Ea8 | ABX11258 | Huang et al | 2007 | Bt HZM2 | |
| Cry1Eb1 | AAA22346 | Feitelson | 1993 | Bt aizawai PS81A2 | |
| Cry1Fa1 | AAA22348 | Chambers et al | 1991 | Bt aizawai EG6346 | |
| Cry1Fa2 | AAA22347 | Feitelson | 1993 | Bt aizawai PS81I | |
| Cry1Fb1 | CAA80235 | Lambert | 1993 | Bt BTS00349A | |
| Cry1Fb2 | BAA25298 | Masuda & Asano | 1998 | Bt morrisoni INA67 | |
| Cry1Fb3 | AAF21767 | Song et al | 1998 | Bt morrisoni | |
| Cry1Fb4 | AAC10641 | Payne et al | 1997 | | |
| Cry1Fb5 | AAO13295 | Li et al | 2001 | Bt B-Pr-88 | |
| Cry1Fb6 | ACD50892 | Huang et al | 2008 | Bt 012 | |
| Cry1Fb7 | ACD50893 | Huang et al | 2008 | Bt 087 | |
| Cry1Ga1 | CAA80233 | Lambert | 1993 | Bt BTS0349A | |
| Cry1Ga2 | CAA70506 | Shevelev et al | 1997 | Bt wuhanensis | |
| Cry1Gb1 | AAD10291 | Kuo & Chak | 1999 | Bt wuhanensis HD525 | |
| Cry1Gb2 | AAO13756 | Li et al | 2000 | Bt B-Pr-88 | |
| Cry1Gc | AAQ52381 | Baum et al | 2003 | | |
| Cry1Ha1 | CAA80236 | Lambert | 1993 | Bt BTS02069AA | |
| Cry1Hb1 | AAA79694 | Koo et al | 1995 | Bt morrisoni BF190 | |
| Cry1H-like | AAF01213 | Srifah et al | 1999 | Bt JC291 | insufficient sequence |
| Cry1Ia1 | CAA44633 | Tailor et al | 1992 | Bt kurstaki | |
| Cry1Ia2 | AAA22354 | Gleave et al | 1993 | Bt kurstaki | |
| Cry1Ia3 | AAC36999 | Shin et al | 1995 | Bt kurstaki HD1 | |
| Cry1Ia4 | AAB00958 | Kostichka et al | 1996 | Bt AB88 | |
| Cry1Ia5 | CAA70124 | Selvapandiyan | 1996 | Bt 61 | |
| Cry1Ia6 | AAC26910 | Zhong et al | 1998 | Bt kurstaki S101 | |
| Cry1Ia7 | AAM73516 | Porcar et al | 2000 | Bt | |
| Cry1Ia8 | AAK66742 | Song et al | 2001 | | |
| Cry1Ia9 | AAQ08616 | Yao et al | 2002 | Bt Ly30 | |
| Cry1Ia10 | AAP86782 | Espindola et al | 2003 | Bt thuringiensis | |
| Cry1Ia11 | CAC85964 | Tounsi et al | 2003 | Bt kurstaki BNS3 | |
| Cry1Ia12 | AAV53390 | Grossi de Sa et al | 2005 | Bt | |

APPENDIX A-continued

List of delta-endotoxins—from Crickmore et al website (cited in application)
Accession Number is to NCBI entry (if available)

| Name | Accession | Authors | Year | Strain | Notes |
|---|---|---|---|---|---|
| Cry1Ia13 | ABF83202 | Martins et al | 2006 | Bt | |
| Cry1Ia14 | ACG63871 | Liu & Guo | 2008 | Bt11 | |
| Cry1Ia15 | FJ617445 | Guan Peng et al | 2009 | Bt E-1B | No NCBI link July 2009 |
| Cry1Ia16 | FJ617448 | Guan Peng et al | 2009 | Bt E-1A | No NCBI link July 2009 |
| Cry1Ib1 | AAA82114 | Shin et al | 1995 | Bt entomocidus BP465 | |
| Cry1Ib2 | ABW88019 | Guan et al | 2007 | Bt PP61 | |
| Cry1Ib3 | ACD75515 | Liu & Guo | 2008 | Bt GS8 | |
| Cry1Ic1 | AAC62933 | Osman et al | 1998 | Bt C18 | |
| Cry1Ic2 | AAE71691 | Osman et al | 2001 | | |
| Cry1Id1 | AAD44366 | Choi | 2000 | | |
| Cry1Ie1 | AAG43526 | Song et al | 2000 | Bt BTC007 | |
| Cry1If1 | AAQ52382 | Baum et al | 2003 | | |
| Cry1I-like | AAC31094 | Payne et al | 1998 | | insufficient sequence |
| Cry1I-like | ABG88859 | Lin & Fang | 2006 | Bt ly4a3 | insufficient sequence |
| Cry1Ja1 | AAA22341 | Donovan | 1994 | Bt EG5847 | |
| Cry1Jb1 | AAA98959 | Von Tersch & Gonzalez | 1994 | Bt EG5092 | |
| Cry1Jc1 | AAC31092 | Payne et al | 1998 | | |
| Cry1Jc2 | AAQ52372 | Baum et al | 2003 | | |
| Cry1Jd1 | CAC50779 | Arnaut et al | 2001 | Bt | |
| Cry1Ka1 | AAB00376 | Koo et al | 1995 | Bt morrisoni BF190 | |
| Cry1La1 | AAS60191 | Je et al | 2004 | Bt kurstaki K1 | |
| Cry1-like | AAC31091 | Payne et al | 1998 | | insufficient sequence |
| Cry2Aa1 | AAA22335 | Donovan et al | 1989 | Bt kurstaki | |
| Cry2Aa2 | AAA83516 | Widner & Whiteley | 1989 | Bt kurstaki HD1 | |
| Cry2Aa3 | D86064 | Sasaki et al | 1997 | Bt sotto | DNA sequence only |
| Cry2Aa4 | AAC04867 | Misra et al | 1998 | Bt kenyae HD549 | |
| Cry2Aa5 | CAA10671 | Yu & Pang | 1999 | Bt SL39 | |
| Cry2Aa6 | CAA10672 | Yu & Pang | 1999 | Bt YZ71 | |
| Cry2Aa7 | CAA10670 | Yu & Pang | 1999 | Bt CY29 | |
| Cry2Aa8 | AAO13734 | Wei et al | 2000 | Bt Dongbei 66 | |
| Cry2Aa9 | AAO13750 | Zhang et al | 2000 | | |
| Cry2Aa10 | AAQ04263 | Yao et al | 2001 | | |
| Cry2Aa11 | AAQ52384 | Baum et al | 2003 | | |
| Cry2Aa12 | ABI83671 | Tan et al | 2006 | Bt Rpp39 | |
| Cry2Aa13 | ABL01536 | Arango et al | 2008 | Bt 146-158-01 | |
| Cry2Aa14 | ACF04939 | Hire et al | 2008 | Bt HD-550 | |
| Cry2Ab1 | AAA22342 | Widner & Whiteley | 1989 | Bt kurstaki HD1 | |
| Cry2Ab2 | CAA39075 | Dankocsik et al | 1990 | Bt kurstaki HD1 | |
| Cry2Ab3 | AAG36762 | Chen et al | 1999 | Bt BTC002 | |
| Cry2Ab4 | AAO13296 | Li et al | 2001 | Bt B-Pr-88 | |
| Cry2Ab5 | AAQ04609 | Yao et al | 2001 | Bt ly30 | |
| Cry2Ab6 | AAP59457 | Wang et al | 2003 | Bt WZ-7 | |
| Cry2Ab7 | AAZ66347 | Udayasuriyan et al | 2005 | Bt 14-1 | |
| Cry2Ab8 | ABC95996 | Huang et al | 2006 | Bt WB2 | |
| Cry2Ab9 | ABC74968 | Zhang et al | 2005 | Bt LLB6 | |
| Cry2Ab10 | EF157306 | Lin et al | 2006 | Bt LyD | |
| Cry2Ab11 | CAM84575 | Saleem et al | 2007 | Bt CMBL-BT1 | |
| Cry2Ab12 | ABM21764 | Lin et al | 2007 | Bt LyD | |
| Cry2Ab13 | ACG76120 | Zhu et al | 2008 | Bt ywc5-4 | |
| Cry2Ab14 | ACG76121 | Zhu et al | 2008 | Bt Bts | |
| Cry2Ac1 | CAA40536 | Aronson | 1991 | Bt shanghai S1 | |
| Cry2Ac2 | AAG35410 | Song et al | 2000 | | |
| Cry2Ac3 | AAQ52385 | Baum et al | 2003 | | |
| Cry2Ac4 | ABC95997 | Huang et al | 2006 | Bt WB9 | |
| Cry2Ac5 | ABC74969 | Zhang et al | 2005 | | |
| Cry2Ac6 | ABC74793 | Xia et al | 2006 | Bt wuhanensis | |
| Cry2Ac7 | CAL18690 | Saleem et al | 2008 | Bt SBSBT-1 | |
| Cry2Ac8 | CAM09325 | Saleem et al | 2007 | Bt CMBL-BT1 | |
| Cry2Ac9 | CAM09326 | Saleem et al | 2007 | Bt CMBL-BT2 | |
| Cry2Ac10 | ABN15104 | Bai et al | 2007 | Bt QCL-1 | |
| Cry2Ac11 | CAM83895 | Saleem et al | 2007 | Bt HD29 | |
| Cry2Ac12 | CAM83896 | Saleem et al | 2007 | Bt CMBL-BT3 | |
| Cry2Ad1 | AAF09583 | Choi et al | 1999 | Bt BR30 | |
| Cry2Ad2 | ABC86927 | Huang et al | 2006 | Bt WB10 | |
| Cry2Ad3 | CAK29504 | Saleem et al | 2006 | Bt 5_2AcT(1) | |
| Cry2Ad4 | CAM32331 | Saleem et al | 2007 | Bt CMBL-BT2 | |
| Cry2Ad5 | CAO78739 | Saleem et al | 2007 | Bt HD29 | |
| Cry2Ae1 | AAQ52362 | Baum et al | 2003 | | |
| Cry2Af1 | ABO30519 | Beard et al | 2007 | Bt C81 | |
| Cry2Ag | ACH91610 | Zhu et al | 2008 | Bt JF19-2 | |
| Cry2Ah | EU939453 | Zhang et al | 2008 | Bt | No NCBI link July 2009 |
| Cry2Ah2 | ACL80665 | Zhang et al | 2009 | Bt BRC-ZQL3 | |
| Cry2Ai | FJ788388 | Udayasuriyan et al | 2009 | Bt | No NCBI link July 2009 |
| Cry3Aa1 | AAA22336 | Herrnstadt et al | 1987 | Bt san diego | |
| Cry3Aa2 | AAA22541 | Sekar et al | 1987 | Bt tenebrionis | |
| Cry3Aa3 | CAA68482 | Hofte et al | 1987 | | |
| Cry3Aa4 | AAA22542 | McPherson et al | 1988 | Bt tenebrionis | |

APPENDIX A-continued

List of delta-endotoxins—from Crickmore et al. website (cited in application)
Accession Number is to NCBI entry (if available)

| Name | Accession | Authors | Year | Strain | Notes |
|---|---|---|---|---|---|
| Cry3Aa5 | AAA50255 | Donovan et al | 1988 | Bt morrisoni EG2158 | |
| Cry3Aa6 | AAC43266 | Adams et al | 1994 | Bt tenebrionis | |
| Cry3Aa7 | CAB41411 | Zhang et al | 1999 | Bt 22 | |
| Cry3Aa8 | AAS79487 | Gao and Cai | 2004 | Bt YM-03 | |
| Cry3Aa9 | AAW05659 | Bulla and Candas | 2004 | Bt UTD-001 | |
| Cry3Aa10 | AAU29411 | Chen et al | 2004 | Bt 886 | |
| Cry3Aa11 | AAW82872 | Kurt et al | 2005 | Bt tenebrionis Mm2 | |
| Cry3Aa12 | ABY49136 | Sezen et al | 2008 | Bt tenebrionis | |
| Cry3Ba1 | CAA34983 | Sick et al | 1990 | Bt tolworthi 43F | |
| Cry3Ba2 | CAA00645 | Peferoen et al | 1990 | Bt PGSI208 | |
| Cry3Bb1 | AAA22334 | Donovan et al | 1992 | Bt EG4961 | |
| Cry3Bb2 | AAA74198 | Donovan et al | 1995 | Bt EG5144 | |
| Cry3Bb3 | I15475 | Peferoen et al | 1995 | | DNA sequence only |
| Cry3Ca1 | CAA42469 | Lambert et al | 1992 | Bt kurstaki BtI109P | |
| Cry4Aa1 | CAA68485 | Ward & Ellar | 1987 | Bt israelensis | |
| Cry4Aa2 | BAA00179 | Sen et al | 1988 | Bt israelensis HD522 | |
| Cry4Aa3 | CAD30148 | Berry et al | 2002 | Bt israelensis | |
| Cry4A-like | AAY96321 | Mahalakshmi et al | 2005 | Bt LDC-9 | insufficient sequence |
| Cry4Ba1 | CAA30312 | Chungjatpornchai et al | 1988 | Bt israelensis 4Q2-72 | |
| Cry4Ba2 | CAA30114 | Tungpradubkul et al | 1988 | Bt israelensis | |
| Cry4Ba3 | AAA22337 | Yamamoto et al | 1988 | Bt israelensis | |
| Cry4Ba4 | BAA00178 | Sen et al | 1988 | Bt israelensis HD522 | |
| Cry4Ba5 | CAD30095 | Berry et al | 2002 | Bt israelensis | |
| Cry4Ba-like | ABC47686 | Mahalakshmi et al | 2005 | Bt LDC-9 | insufficient sequence |
| Cry4Ca1 | EU646202 | Shu et al | 2008 | | No NCBI link July 2009 |
| Cry4Cb1 | FJ403208 | Jun & Furong | 2008 | Bt HS18-1 | No NCBI link July 2009 |
| Cry4Cb2 | FJ597622 | Jun & Furong | 2008 | BT Ywc2-8 | No NCBI link July 2009 |
| Cry4Cc1 | FJ403207 | Jun & Furong | 2008 | Bt MC28 | No NCBI link July 2009 |
| Cry5Aa1 | AAA67694 | Narva et al | 1994 | Bt darmstadiensis PS17 | |
| Cry5Ab1 | AAA67693 | Narva et al | 1991 | Bt darmstadiensis PS17 | |
| Cry5Ac1 | I34543 | Payne et al | 1997 | | DNA sequence only |
| Cry5Ad1 | ABQ82087 | Lenane et al | 2007 | Bt L366 | |
| Cry5Ba1 | AAA68598 | Foncerrada & Narva | 1997 | Bt PS86Q3 | |
| Cry5Ba2 | ABW88931 | Guo et al | 2008 | YBT 1518 | |
| Cry6Aa1 | AAA22357 | Narva et al | 1993 | Bt PS52A1 | |
| Cry6Aa2 | AAM46849 | Bai et al | 2001 | YBT 1518 | |
| Cry6Aa3 | ABH03377 | Jia et al | 2006 | Bt 96418 | |
| Cry6Ba1 | AAA22358 | Narva et al | 1991 | Bt PS69D1 | |
| Cry7Aa1 | AAA22351 | Lambert et al | 1992 | Bt galleriae PGSI245 | |
| Cry7Ab1 | AAA21120 | Narva & Fu | 1994 | Bt dakota HD511 | |
| Cry7Ab2 | AAA21121 | Narva & Fu | 1994 | Bt kumamotoensis 867 | |
| Cry7Ab3 | ABX24522 | Song et al | 2008 | Bt WZ-9 | |
| Cry7Ab4 | EU380678 | Shu et al | 2008 | Bt | No NCBI link July 2009 |
| Cry7Ab5 | ABX79555 | Aguirre-Arzola et al | 2008 | Bt monterrey GM-33 | |
| Cry7Ab6 | ACI44005 | Deng et al | 2008 | Bt HQ122 | |
| Cry7Ab7 | FJ940776 | Wang et al | 2009 | | No NCBI link September 2009 |
| Cry7Ab8 | GU145299 | Feng Jing | 2009 | | No NCBI link November 2009 |
| Cry7Ba1 | ABB70817 | Zhang et al | 2006 | Bt huazhongensis | |
| Cry7Ca1 | ABR67863 | Gao et al | 2007 | Bt BTH-13 | |
| Cry7Da1 | ACQ99547 | Yi et al | 2009 | Bt LH-2 | |
| Cry8Aa1 | AAA21117 | Narva & Fu | 1992 | Bt kumamotoensis | |
| Cry8Ab1 | EU044830 | Cheng et al | 2007 | Bt B-JJX | No NCBI link July 2009 |
| Cry8Ba1 | AAA21118 | Narva & Fu | 1993 | Bt kumamotoensis | |
| Cry8Bb1 | CAD57542 | Abad et al | 2002 | | |
| Cry8Bc1 | CAD57543 | Abad et al | 2002 | | |
| Cry8Ca1 | AAA21119 | Sato et al. | 1995 | Bt japonensis Buibui | |
| Cry8Ca2 | AAR98783 | Shu et al | 2004 | Bt HBF-1 | |
| Cry8Ca3 | EU625349 | Du et al | 2008 | Bt FTL-23 | No NCBI link July 2009 |
| Cry8Da1 | BAC07226 | Asano et al | 2002 | Bt galleriae | |
| Cry8Da2 | BD133574 | Asano et al | 2002 | Bt | DNA sequence only |
| Cry8Da3 | BD133575 | Asano et al | 2002 | Bt | DNA sequence only |
| Cry8Db1 | BAF93483 | Yamaguchi et al | 2007 | Bt BBT2-5 | |
| Cry8Ea1 | AAQ73470 | Fuping et al | 2003 | Bt 185 | |
| Cry8Ea2 | EU047597 | Liu et al | 2007 | Bt B-DLL | No NCBI link July 2009 |
| Cry8Fa1 | AAT48690 | Shu et al | 2004 | Bt 185 | also AAW81032 |
| Cry8Ga1 | AAT46073 | Shu et al | 2004 | Bt HBF-18 | |
| Cry8Ga2 | ABC42043 | Yan et al | 2008 | Bt 145 | |
| Cry8Ga3 | FJ198072 | Xiaodong et al | 2008 | Bt FCD114 | No NCBI link July 2009 |
| Cry8Ha1 | EF465532 | Fuping et al | 2006 | Bt 185 | No NCBI link July 2009 |
| Cry8Ia1 | EU381044 | Yan et al | 2008 | Bt su4 | No NCBI link July 2009 |
| Cry8Ja1 | EU625348 | Du et al | 2008 | Bt FPT-2 | No NCBI link July 2009 |
| Cry8Ka1 | FJ422558 | Quezado et al | 2008 | | No NCBI link July 2009 |
| Cry8Ka2 | ACN87262 | Noguera & Ibarra | 2009 | Bt kenyae | |
| Cry8-like | FJ770571 | Noguera & Ibarra | 2009 | Bt canadensis | DNA sequence only |
| Cry8-like | ABS53003 | Mangena et al | 2007 | Bt | |
| Cry9Aa1 | CAA41122 | Shevelev et al | 1991 | Bt galleriae | |
| Cry9Aa2 | CAA41425 | Gleave et al | 1992 | Bt DSIR517 | |

APPENDIX A-continued

List of delta-endotoxins—from Crickmore et al. website (cited in application)
Accession Number is to NCBI entry (if available)

| | | | | | |
|---|---|---|---|---|---|
| Cry9Aa3 | GQ249293 | Su et al | 2009 | Bt SC5(D2) | No NCBI link July 2009 |
| Cry9Aa4 | GQ249294 | Su et al | 2009 | Bt T03C001 | No NCBI link July 2009 |
| Cry9Aa like | AAQ52376 | Baum et al | 2003 | | incomplete sequence |
| Cry9Ba1 | CAA52927 | Shevelev et al | 1993 | Bt galleriae | |
| Cry9Bb1 | AAV28716 | Silva-Werneck et al | 2004 | Bt japonensis | |
| Cry9Ca1 | CAA85764 | Lambert et al | 1996 | Bt tolworthi | |
| Cry9Ca2 | AAQ52375 | Baum et al | 2003 | | |
| Cry9Da1 | BAA19948 | Asano | 1997 | Bt japonensis N141 | |
| Cry9Da2 | AAB97923 | Wasano & Ohba | 1998 | Bt japonensis | |
| Cry9Da3 | GQ249295 | Su et al | 2009 | Bt T03B001 | No NCBI link July 2009 |
| Cry9Da4 | GQ249297 | Su et al | 2009 | Bt T03B001 | No NCBI link July 2009 |
| Cry9Db1 | AAX78439 | Flannagan & Abad | 2005 | Bt kurstaki DP1019 | |
| Cry9Ea1 | BAA34908 | Midoh & Oyama | 1998 | Bt aizawai SSK-10 | |
| Cry9Ea2 | AAO12908 | Li et al | 2001 | Bt B-Hm-16 | |
| Cry9Ea3 | ABM21765 | Lin et al | 2006 | Bt lyA | |
| Cry9Ea4 | ACE88267 | Zhu et al | 2008 | Bt ywc5-4 | |
| Cry9Ea5 | ACF04743 | Zhu et al | 2008 | Bts | |
| Cry9Ea6 | ACG63872 | Liu & Guo | 2008 | Bt 11 | |
| Cry9Ea7 | FJ380927 | Sun et al | 2008 | | No NCBI link July 2009 |
| Cry9Ea8 | GQ249292 | Su et al | 2009 | GQ249292 | No NCBI link July 2009 |
| Cry9Eb1 | CAC50780 | Arnaut et al | 2001 | | |
| Cry9Eb2 | GQ249298 | Su et al | 2009 | Bt T03B001 | No NCBI link July 2009 |
| Cry9Ec1 | AAC63366 | Wasano et al | 2003 | Bt galleriae | |
| Cry9Ed1 | AAX78440 | Flannagan & Abad | 2005 | Bt kurstaki DP1019 | |
| Cry9Ee1 | GQ249296 | Su et al | 2009 | Bt T03B001 | No NCBI link August 2009 |
| Cry9-like | AAC63366 | Wasano et al | 1998 | Bt galleriae | insufficient sequence |
| Cry10Aa1 | AAA22614 | Thorne et al | 1986 | Bt israelensis | |
| Cry10Aa2 | E00614 | Aran & Toomasu | 1996 | Bt israelensis ONR-60A | DNA sequence only |
| Cry10Aa3 | CAD30098 | Berry et al | 2002 | Bt israelensis | |
| Cry10A-like | DQ167578 | Mahalakshmi et al | 2006 | Bt LDC-9 | incomplete sequence |
| Cry11Aa1 | AAA22352 | Donovan et al | 1988 | Bt israelensis | |
| Cry11Aa2 | AAA22611 | Adams et al | 1989 | Bt israelensis | |
| Cry11Aa3 | CAD30081 | Berry et al | 2002 | Bt israelensis | |
| Cry11Aa-like | DQ166531 | Mahalakshmi et al | 2007 | Bt LDC-9 | incomplete sequence |
| Cry11Ba1 | CAA60504 | Delecluse et al | 1995 | Bt jegathesan 367 | |
| Cry11Bb1 | AAC97162 | Orduz et al | 1998 | Bt medellin | |
| Cry12Aa1 | AAA22355 | Narva et al | 1991 | Bt PS33F2 | |
| Cry13Aa1 | AAA22356 | Narva et al | 1992 | Bt PS63B | |
| Cry14Aa1 | AAA21516 | Narva et al | 1994 | Bt sotto PS80JJ1 | |
| Cry15Aa1 | AAA22333 | Brown & Whiteley | 1992 | Bt thompsoni | |
| Cry16Aa1 | CAA63860 | Barloy et al | 1996 | Cb malaysia CH18 | |
| Cry17Aa1 | CAA67841 | Barloy et al | 1998 | Cb malaysia CH18 | |
| Cry18Aa1 | CAA67506 | Zhang et al | 1997 | Paenibacillus popilliae | |
| Cry18Ba1 | AAF89667 | Patel et al | 1999 | Paenibacillus popilliae | |
| Cry18Ca1 | AAF89668 | Patel et al | 1999 | Paenibacillus popilliae | |
| Cry19Aa1 | CAA68875 | Rosso & Delecluse | 1996 | Bt jegathesan 367 | |
| Cry19Ba1 | BAA32397 | Hwang et al | 1998 | Bt higo | |
| Cry20Aa1 | AAB93476 | Lee & Gill | 1997 | Bt fukuokaensis | |
| Cry20Ba1 | ACS93601 | Noguera & Ibarra | 2009 | Bt higo LBIT-976 | |
| Cry20-like | GQ144333 | Yi et al | 2009 | Bt Y-5 | DNA sequence only |
| Cry21Aa1 | I32932 | Payne et al | 1996 | | DNA sequence only |
| Cry21Aa2 | I66477 | Feitelson | 1997 | | DNA sequence only |
| Cry21Ba1 | BAC06484 | Sato & Asano | 2002 | Bt roskildiensis | |
| Cry22Aa1 | I34547 | Payne et al | 1997 | | DNA sequence only |
| Cry22Aa2 | CAD43579 | Isaac et al | 2002 | Bt | |
| Cry22Aa3 | ACD93211 | Du et al | 2008 | Bt FZ-4 | |
| Cry22Ab1 | AAK50456 | Baum et al | 2000 | Bt EG4140 | |
| Cry22Ab2 | CAD43577 | Isaac et al | 2002 | Bt | |
| Cry22Ba1 | CAD43578 | Isaac et al | 2002 | Bt | |
| Cry23Aa1 | AAF76375 | Donovan et al | 2000 | Bt | Binary with Cry37Aa1 |
| Cry24Aa1 | AAC61891 | Kawalek and Gill | 1998 | Bt jegathesan | |
| Cry24Ba1 | BAD32657 | Ohgushi et al | 2004 | Bt sotto | |
| Cry24Ca1 | CAJ43600 | Beron & Salerno | 2005 | Bt FCC-41 | |
| Cry25Aa1 | AAC61892 | Kawalek and Gill | 1998 | Bt jegathesan | |
| Cry26Aa1 | AAD25075 | Wojciechowska et al | 1999 | Bt finitimus B-1166 | |
| Cry27Aa1 | BAA82796 | Saitoh | 1999 | Bt higo | |
| Cry28Aa1 | AAD24189 | Wojciechowska et al | 1999 | Bt finitimus B-1161 | |
| Cry28Aa2 | AAG00235 | Moore and Debro | 2000 | Bt finitimus | |
| Cry29Aa1 | CAC80985 | Delecluse et al | 2000 | Bt medellin | |
| Cry30Aa1 | CAC80986 | Delecluse et al | 2000 | Bt medellin | |
| Cry30Ba1 | BAD00052 | Ito et al | 2003 | Bt entomocidus | |
| Cry30Ca1 | BAD67157 | Ohgushi et al | 2004 | Bt sotto | |
| Cry30Ca2 | ACU24781 | Sun and Park | 2009 | Bt jegathesan 367 | |
| Cry30Da1 | EF095955 | Shu et al | 2006 | Bt Y41 | No NCBI link July 2009 |
| Cry30Db1 | BAE80088 | Kishida et al | 2006 | Bt aizawai BUN1-14 | |
| Cry30Ea1 | ACC95445 | Fang et al | 2007 | Bt S2160-1 | |
| Cry30Ea2 | FJ499389 | Jun et al | 2008 | Bt Ywc2-8 | No NCBI link July 2009 |

APPENDIX A-continued

List of delta-endotoxins—from Crickmore et al. website (cited in application)
Accession Number is to NCBI entry (if available)

| Name | Accession | Authors | Year | Source | Notes |
|---|---|---|---|---|---|
| Cry30Fa1 | ACI22625 | Tan et al | 2008 | Bt MC28 | |
| Cry30Ga1 | ACG60020 | Zhu et al | 2008 | Bt HS18-1 | |
| Cry31Aa1 | BAB11757 | Saitoh & Mizuki | 2000 | Bt 84-HS-1-11 | |
| Cry31Aa2 | AAL87458 | Jung and Cote | 2000 | Bt M15 | |
| Cry31Aa3 | BAE79808 | Uemori et al | 2006 | Bt B0195 | |
| Cry31Aa4 | BAF32571 | Yasutake et al | 2006 | Bt 79-25 | |
| Cry31Aa5 | BAF32572 | Yasutake et al | 2006 | Bt 92-10 | |
| Cry31Ab1 | BAE79809 | Uemori et al | 2006 | Bt B0195 | |
| Cry31Ab2 | BAF32570 | Yasutake et al | 2006 | Bt 31-5 | |
| Cry31Ac1 | BAF34368 | Yasutake et al | 2006 | Bt 87-29 | |
| Cry32Aa1 | AAG36711 | Balasubramanian et al | 2001 | Bt yunnanensis | |
| Cry32Ba1 | BAB78601 | Takebe et al | 2001 | Bt | |
| Cry32Ca1 | BAB78602 | Takebe et al | 2001 | Bt | |
| Cry32Da1 | BAB78603 | Takebe et al | 2001 | Bt | |
| Cry33Aa1 | AAL26871 | Kim et al | 2001 | Bt dakota | |
| Cry34Aa1 | AAG50341 | Ellis et al | 2001 | Bt PS80JJ1 | Binary with Cry35Aa1 |
| Cry34Aa2 | AAK64560 | Rupar et al | 2001 | Bt EG5899 | Binary with Cry35Aa2 |
| Cry34Aa3 | AAT29032 | Schnepf et al | 2004 | Bt PS69Q | Binary with Cry35Aa3 |
| Cry34Aa4 | AAT29030 | Schnepf et al | 2004 | Bt PS185GG | Binary with Cry35Aa4 |
| Cry34Ab1 | AAG41671 | Moellenbeck et al | 2001 | Bt PS149B1 | Binary with Cry35Ab1 |
| Cry34Ac1 | AAG50118 | Ellis et al | 2001 | Bt PS167H2 | Binary with Cry35Ac1 |
| Cry34Ac2 | AAK64562 | Rupar et al | 2001 | Bt EG9444 | Binary with Cry35Ab2 |
| Cry34Ac3 | AAT29029 | Schnepf et al | 2004 | Bt KR1369 | Binary with Cry35Ab3 |
| Cry34Ba1 | AAK64565 | Rupar et al | 2001 | Bt EG4851 | Binary with Cry35Ba1 |
| Cry34Ba2 | AAT29033 | Schnepf et al | 2004 | Bt PS201L3 | Binary with Cry35Ba2 |
| Cry34Ba3 | AAT29031 | Schnepf et al | 2004 | Bt PS201HH2 | Binary with Cry35Ba3 |
| Cry35Aa1 | AAG50342 | Ellis et al | 2001 | Bt PS80JJ1 | Binary with Cry34Aa1 |
| Cry35Aa2 | AAK64561 | Rupar et al | 2001 | Bt EG5899 | Binary with Cry34Aa2 |
| Cry35Aa3 | AAT29028 | Schnepf et al | 2004 | Bt PS69Q | Binary with Cry34Aa3 |
| Cry35Aa4 | AAT29025 | Schnepf et al | 2004 | Bt PS185GG | Binary with Cry34Aa4 |
| Cry35Ab1 | AAG41672 | Moellenbeck et al | 2001 | Bt PS149B1 | Binary with Cry34Ab1 |
| Cry35Ab2 | AAK64563 | Rupar et al | 2001 | Bt EG9444 | Binary with Cry34Ac2 |
| Cry35Ab3 | AY536891 AAT29024 | | 2004 | Bt KR1369 | Binary with Cry34Ab3 |
| Cry35Ac1 | AAG50117 | Ellis et al | 2001 | Bt PS167H2 | Binary with Cry34Ac1 |
| Cry35Ba1 | AAK64566 | Rupar et al | 2001 | Bt EG4851 | Binary with Cry34Ba1 |
| Cry35Ba2 | AAT29027 | Schnepf et al | 2004 | Bt PS201L3 | Binary with Cry34Ba2 |
| Cry35Ba3 | AAT29026 | Schnepf et al | 2004 | Bt PS201HH2 | Binary with Cry34Ba3 |
| Cry36Aa1 | AAK64558 | Rupar et al | 2001 | Bt | |
| Cry37Aa1 | AAF76376 | Donovan et al | 2000 | Bt | Binary with Cry23Aa |
| Cry38Aa1 | AAK64559 | Rupar et al | 2000 | Bt | |
| Cry39Aa1 | BAB72016 | Ito et al | 2001 | Bt aizawai | |
| Cry40Aa1 | BAB72018 | Ito et al | 2001 | Bt aizawai | |
| Cry40Ba1 | BAC77648 | Ito et al | 2003 | Bun1-14 | |
| Cry40Ca1 | EU381045 | Shu et al | 2008 | Bt Y41 | No NCBI link July 2009 |
| Cry40Da1 | ACF15199 | Zhang et al | 2008 | Bt S2096-2 | |
| Cry41Aa1 | BAD35157 | Yamashita et al | 2003 | Bt A1462 | |
| Cry41Ab1 | BAD35163 | Yamashita et al | 2003 | Bt A1462 | |
| Cry42Aa1 | BAD35166 | Yamashita et al | 2003 | Bt A1462 | |
| Cry43Aa1 | BAD15301 | Yokoyama and Tanaka | 2003 | P. lentimorbus semadara | |
| Cry43Aa2 | BAD95474 | Nozawa | 2004 | P. popilliae popilliae | |
| Cry43Ba1 | BAD15303 | Yokoyama and Tanaka | 2003 | P. lentimorbus semadara | |
| Cry43-like | BAD15305 | Yokoyama and Tanaka | 2003 | P. lentimorbus semadara | |
| Cry44Aa | BAD08532 | Ito et al | 2004 | Bt entomocidus INA288 | |
| Cry45Aa | BAD22577 | Okumura et al | 2004 | Bt 89-T-34-22 | |
| Cry46Aa | BAC79010 | Ito et al | 2004 | Bt dakota | |
| Cry46Aa2 | BAG68906 | Ishikawa et al | 2008 | Bt A1470 | |
| Cry46Ab | BAD35170 | Yamagiwa et al | 2004 | Bt | |
| Cry47Aa | AAY24695 | Kongsuwan et al | 2005 | Bt CAA890 | |
| Cry48Aa | CAJ18351 | Jones and Berry | 2005 | Bs IAB59 | binary with 49Aa |
| Cry48Aa2 | CAJ86545 | Jones and Berry | 2006 | Bs 47-6B | binary with 49Aa2 |
| Cry48Aa3 | CAJ86546 | Jones and Berry | 2006 | Bs NHA15b | binary with 49Aa3 |
| Cry48Ab | CAJ86548 | Jones and Berry | 2006 | Bs LP1G | binary with 49Ab1 |
| Cry48Ab2 | CAJ86549 | Jones and Berry | 2006 | Bs 2173 | binary with 49Aa4 |
| Cry49Aa | CAH56541 | Jones and Berry | 2005 | Bs IAB59 | binary with 48Aa |
| Cry49Aa2 | CAJ86541 | Jones and Berry | 2006 | Bs 47-6B | binary with 48Aa2 |
| Cry49Aa3 | CAJ86543 | Jones and Berry | 2006 | BsNHA15b | binary with 48Aa3 |
| Cry49Aa4 | CAJ86544 | Jones and Berry | 2006 | Bs 2173 | binary with 48Ab2 |
| Cry49Ab1 | CAJ86542 | Jones and Berry | 2006 | Bs LP1G | binary with 48Ab1 |
| Cry50Aa1 | BAE86999 | Ohgushi et al | 2006 | Bt sotto | |
| Cry51Aa1 | ABI14444 | Meng et al | 2006 | Bt F14-1 | |
| Cry52Aa1 | EF613489 | Song et al | 2007 | Bt Y41 | No NCBI link July 2009 |
| Cry52Ba1 | FJ361760 | Jun et al | 2008 | Bt BM59-2 | No NCBI link July 2009 |
| Cry53Aa1 | EF633476 | Song et al | 2007 | Bt Y41 | No NCBI link July 2009 |
| Cry53Ab1 | FJ361759 | Jun et al | 2008 | Bt MC28 | No NCBI link July 2009 |
| Cry54Aa1 | ACA52194 | Tan et al | 2009 | Bt MC28 | |
| Cry55Aa1 | ABW88932 | Guo et al | 2008 | YBT 1518 | |
| Cry55Aa2 | AAE33526 | Bradfisch et al | 2000 | BT Y41 | |

APPENDIX A-continued

List of delta-endotoxins—from Crickmore et al. website (cited in application)
Accession Number is to NCBI entry (if available)

| | | | | | | | |
|---|---|---|---|---|---|---|---|
| Cry56Aa1 | | FJ597621 | Jun & Furong | 2008 | Bt Ywc2-8 | | No NCBI link July 2009 |
| Cry56Aa2 | | GQ483512 | Guan Peng et al | 2009 | Bt G7-1 | | No NCBI link August 2009 |
| Cry57Aa1 | | ANC87261 | Noguera & Ibarra | 2009 | Bt kim | | |
| Cry58Aa1 | | ANC87260 | Noguera & Ibarra | 2009 | Bt entomocidus | | |
| Cry59Aa1 | | ACR43758 | Noguera & Ibarra | 2009 | Bt kim LBIT-980 | | |
| Vip3Aa1 | Vip3Aa | AAC37036 | Estruch et al | 1996 | PNAS 93, 5389-5394 | AB88 | |
| Vip3Aa2 | Vip3Ab | AAC37037 | Estruch et al | 1996 | PNAS 93, 5389-5394 | AB424 | |
| Vip3Aa3 | Vip3Ac | | Estruch et al | 2000 | U.S. Pat. No. 6,137,033 October 2000 | | |
| Vip3Aa4 | PS36A Sup | AAR81079 | Feitelson et al | 1998 | U.S. Pat. No. 6,656,908 December 2003 | Bt PS36A | WO9818932(A2, A3) 7 May 1998 |
| Vip3Aa5 | PS81F Sup | AAR81080 | Feitelson et al | 1998 | U.S. Pat. No. 6,656,908 December 2003 | Bt PS81F | WO9818932(A2, A3) 7 May 1998 |
| Vip3Aa6 | Jav90 Sup | AAR81081 | Feitelson et al | 1998 | U.S. Pat. No. 6,656,908 December 2003 | Bt | WO9818932(A2, A3) 7 May 1998 |
| Vip3Aa7 | Vip83 | AAK95326 | Cai et al | 2001 | unpublished | Bt YBT-833 | |
| Vip3Aa8 | Vip3A | AAK97481 | Loguercio et al | 2001 | unpublished | Bt HD125 | |
| Vip3Aa9 | VipS | CAA76665 | Selvapandiyan et al | 2001 | unpublished | Bt A13 | |
| Vip3Aa10 | Vip3V | AAN60738 | Doss et al | 2002 | Protein Expr. Purif. 26, 82-88 | Bt | |
| Vip3Aa11 | Vip3A | AAR36859 | Liu et al | 2003 | unpublished | Bt C9 | |
| Vip3Aa12 | Vip3A-WB5 | AAM22456 | Wu and Guan | 2003 | unpublished | Bt | |
| Vip3Aa13 | Vip3A | AAL69542 | Chen et al | 2002 | Sheng Wu Gong Cheng Xue Bao 18, 687-692 | Bt S184 | |
| Vip3Aa14 | Vip | AAQ12340 | Polumetla et al | 2003 | unpublished | Bt tolworthi | |
| Vip3Aa15 | Vip3A | AAP51131 | Wu et al | 2004 | unpublished | Bt WB50 | |
| Vip3Aa16 | Vip3LB | AAW65132 | Mesrati et al | 2005 | FEMS Micro Lett 244, 353-358 | Bt | |
| Vip3Aa17 | Jav90 | | Feitelson et al | 1999 | U.S. Pat. No. 6,603,063 August 2003 | Javelin 1990 | WO9957282(A2, A3) 11 Nov. 1999 |
| Vip3Aa18 | | AAX49395 | Cai and Xiao | 2005 | unpublished | Bt 9816C | |
| Vip3Aa19 | Vip3ALD | DQ241674 | Liu et al | 2006 | unpublished | Bt AL | |
| Vip3Aa19 | Vip3A-1 | DQ539887 | Hart et al | 2006 | unpublished | | |
| Vip3Aa20 | Vip3A-2 | DQ539888 | Hart et al | 2006 | unpublished | | |
| Vip3Aa21 | Vip | ABD84410 | Panbangred | 2006 | unpublished | Bt aizawai | |
| Vip3Aa22 | Vip3A-LS1 | AAY41427 | Lu et al | 2005 | unpublished | Bt LS1 | |
| Vip3Aa23 | Vip3A-LS8 | AAY41428 | Lu et al | 2005 | unpublished | Bt LS8 | |
| Vip3Aa24 | | BI 880913 | Song et al | 2007 | unpublished | Bt WZ-7 | |
| Vip3Aa25 | | EF608501 | Hsieh et al | 2007 | unpublished | | |
| Vip3Aa26 | | EU294496 | Shen and Guo | 2007 | unpublished | Bt TF9 | |
| Vip3Aa27 | | EU332167 | Shen and Guo | 2007 | unpublished | Bt 16 | |
| Vip3Aa28 | | FJ494817 | Xiumei Yu | 2008 | unpublished | Bt JF23-8 | |
| Vip3Aa29 | | FJ626674 | Xieumei et al | 2009 | unpublished | Bt JF21-1 | |
| Vip3Aa30 | | FJ626675 | Xieumei et al | 2009 | unpublished | MD2-1 | |
| Vip3Aa31 | | FJ626676 | Xieumei et al | 2009 | unpublished | JF21-1 | |
| Vip3Aa32 | | FJ626677 | Xieumei et al | 2009 | unpublished | MD2-1 | |
| Vip3Ab1 | Vip3B | AAR40284 | Feitelson et al | 1999 | U.S. Pat. No. 6,603,063 August 2003 | Bt KB59A4-6 | WO9957282(A2, A3) 11 Nov. 1999 |
| Vip3Ab2 | Vip3D | AAY88247 | Feng and Shen | 2006 | unpublished | Bt | |
| Vip3Ac1 | PS49C | | Narva et al | . | US application 20040128716 | | |
| Vip3Ad1 | PS158C2 | | Narva et al | . | US application 20040128716 | | |
| Vip3Ad2 | ISP3B | CAI43276 | Van Rie et al | 2005 | unpublished | Bt | |
| Vip3Ae1 | ISP3C | CAI43277 | Van Rie et al | 2005 | unpublished | Bt | |
| Vip3Af1 | ISP3A | CAI43275 | Van Rie et al | 2005 | unpublished | Bt | |
| Vip3Af2 | Vip3C | ADN08753 | Syngenta | . | WO 03/075655 | | |
| Vip3Ag1 | Vip3B | ADN08758 | Syngenta | . | WO 02/078437 | | |

APPENDIX A-continued

List of delta-endotoxins—from Crickmore et al. website (cited in application)
Accession Number is to NCBI entry (if available)

| Vip3Ag2 |  | FJ556803 | Audtho et al | 2008 |  | Bt |
| Vip3Ah1 | Vip3S | DQ832323 | Li and Shen | 2006 | unpublished | Bt |
| Vip3Ba1 |  | AAV70653 | Rang et al | 2004 | unpublished |  |
| Vip3Bb1 | Vip3Z | ADN08760 | Syngenta |  | WO 03/075655 |  |
| Vip3Bb2 |  | EF439819 | Akhurst et al | 2007 |  |  |

We claim:

1. A transgenic plant comprising DNA encoding a Cry1Be insecticidal protein and DNA encoding a Cry1Fa insecticidal protein, wherein said Cry1Fa insecticidal protein is at least 95% identical with SEQ ID NO:1, and said Cry1Be insecticidal protein is at least 95% identical with SEQ ID NO:2, wherein said transgenic plant expresses an effective amount of said Cry1Fa insecticidal protein and said Cry1Be insecticidal protein to prevent development of Cry-resistant lepidopteran pests, and wherein said Cry1Fa insecticidal protein and said Cry1Be insecticidal protein do not share a receptor binding site in European corn borer (ECB) gut and do not share a receptor binding site in fall armyworm (FAW) gut.

2. A seed of the plant of claim 1 comprising DNA encoding said Cry1Be insecticidal protein and DNA encoding said Cry1Fa insecticidal protein.

3. A plurality of plants comprising non-Bt refuge plants and a plurality of transgenic plants of claim 1, wherein said refuge plants comprise less than 40% of all crop plants in said plurality of plants.

4. The plurality of plants of claim 3, wherein said refuge plants are in blocks or strips.

5. A mixture of seeds comprising refuge seeds from non-Bt refuge plants, and a plurality of seeds of claim 2, wherein said refuge seeds comprise less than 40% of all the seeds in the mixture.

6. A method of managing development of resistance to a Cry toxin by an insect, said method comprising planting seeds to produce the plurality of plants of claim 3.

7. A composition for controlling Cry1Fa-resistant lepidopteran pests, said composition comprising cells that express effective amounts of both a Cry1Fa core toxin-containing protein and a Cry1Be core toxin-containing protein, wherein said Cry1Fa core-toxin containing protein and said Cry1Be core toxin-containing insecticidal protein do not share a receptor binding site in ECB gut and do not share a receptor binding site in FAW gut.

8. The composition of claim 7 comprising a host transformed to express both said Cry1Fa protein and said Cry1Be protein, wherein said host is a microorganism or a plant cell.

9. A method of controlling Cry1Fa-resistant lepidopteran pests, said method comprising presenting to said pests or to the environment of said pests an effective amount of the composition of claim 7, wherein said lepidopteran pests are selected from the group consisting of European corn borer and fall armyworm.

10. A transgenic plant that produces four insecticidal proteins derived from *Bacillus thuringiensis*, wherein three of said proteins provide non-cross-resistant activity against a first insect, and three of said proteins provide non-cross-resistant activity against a second insect, wherein said plant comprises DNA encoding a Cry1Fa insecticidal protein and DNA encoding a Cry1Be insecticidal protein, wherein said first insect is European corn borer and said second insect is fall armyworm, and wherein said Cry1Fa insecticidal protein and said Cry1Be insecticidal protein do not share a receptor binding site in ECB gut and do not share a receptor binding site in FAW gut.

11. The transgenic plant of claim 1, wherein the plant produces a third protein selected from the group consisting of Cry1Ab, Cry2Aa, and Cry1I proteins.

12. The transgenic plant of claim 1, wherein the plant produces a third protein selected from the group consisting of Vip3A, Cry1C, Cry1D, and Cry1E proteins.

13. The transgenic plant of claim 11, wherein the plant produces a fourth protein selected from the group consisting of Vip3A, Cry1C, Cry1D, and Cry1E proteins.

14. A method of managing development of resistance to a Cry1Fa toxin by European corn borer and fall armyworm, said method comprising planting seeds to produce the transgenic plant of claim 10.

15. A plurality of plants comprising non-Bt refuge plants and a plurality of the transgenic plants of claim 10, wherein said refuge plants comprise less than about 20% of all crop plants in said plurality of plants.

16. A method of managing development of resistance to a Cry1Fa toxin by European corn borer and fall armyworm, said method comprising planting seeds to produce the plurality of plants of claim 15.

17. A mixture of seeds comprising refuge seeds from non-Bt refuge plants, and a plurality of transgenic seeds from the plant of claim 10, wherein said refuge seeds comprise less than 10% of all the seeds in the mixture.

18. A plant cell of the plant of claim 1, wherein said plant cell comprises said DNA encoding said Cry1Fa insecticidal protein and said DNA encoding said Cry1Be insecticidal protein, wherein said Cry1Fa insecticidal protein is at least 99% identical with SEQ ID NO: 1, and said Cry1Be insecticidal protein is at least 99% identical with SEQ ID NO: 2.

19. The plant of claim 1, wherein said Cry1Fa insecticidal protein comprises SEQ ID NO:1, and said Cry1Be insecticidal protein comprises SEQ ID NO:2.

20. A method of controlling a Cry resistant insect selected from the group consisting of a European corn borer and a fall armyworm, said method comprising contacting said insect with a Cry1Be insecticidal protein and a Cry1Fa insecticidal protein, wherein said Cry1Fa insecticidal protein and said Cry1Be insecticidal protein do not share a receptor binding site in ECB gut and do not share a receptor binding site in FAW gut.

21. A plant cell of the plant of claim 10, wherein said Cry1Fa insecticidal protein is at least 99% identical with SEQ ID NO:1, and said Cry1Be insecticidal protein is at least 99% identical with SEQ ID NO:2.

22. The plant of claim 10, wherein said Cry1Fa insecticidal protein comprises SEQ ID NO:1, and said Cry1Be insecticidal protein comprises SEQ ID NO:2.

* * * * *

SEQUENCE LISTING

<160> NUMBER OF SEQ ID NOS: 2

<210> SEQ ID NO 1
<211> LENGTH: 605
<212> TYPE: PRT
<213> ORGANISM: Artificial Sequence
<220> FEATURE:
<223> OTHER INFORMATION: Cry1Fa

<400> SEQUENCE: 1

```
Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270
```

-continued

```
Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
        435                 440                 445

Thr His Arg Ser Ala Thr Pro Thr Asn Thr Ile Asp Pro Glu Arg Ile
    450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
            500                 505                 510

Pro Gln Arg Tyr Arg Ala Arg Ile Arg Tyr Ala Ser Thr Thr Asn Leu
        515                 520                 525

Arg Ile Tyr Val Thr Val Ala Gly Glu Arg Ile Phe Ala Gly Gln Phe
    530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Leu Glu
        595                 600                 605

<210> SEQ ID NO 2
<211> LENGTH: 641
<212> TYPE: PRT
<213> ORGANISM: Artificial Sequence
<220> FEATURE:
<223> OTHER INFORMATION: Cry1Be

<400> SEQUENCE: 2

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30
```

```
Ala Arg Ile Glu Asp Ser Leu Cys Ile Ala Glu Gly Asn Asn Ile Asp
         35                   40                  45

Pro Phe Val Ser Ala Ser Thr Val Gln Thr Gly Ile Asn Ile Ala Gly
 50                   55                  60

Arg Ile Leu Gly Val Leu Gly Val Pro Phe Ala Gly Gln Ile Ala Ser
 65                   70                  75                  80

Phe Tyr Ser Phe Leu Val Gly Glu Leu Trp Pro Arg Gly Arg Asp Pro
             85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
            115                 120                 125

Asn Ser Phe Arg Ala Tyr Gln Gln Ser Leu Glu Asp Trp Leu Glu Asn
        130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
        210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
        290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Thr Ser Ile Asn Pro
        370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
        435                 440                 445
```

```
Glu Thr Glu Leu Pro Pro Glu Thr Thr Glu Arg Pro Asn Tyr Glu Ser
    450                 455                 460
Tyr Ser His Arg Leu Ser Asn Ile Arg Leu Ile Ser Gly Asn Thr Leu
465                 470                 475                 480
Arg Ala Pro Val Tyr Ser Trp Thr His Arg Ser Ala Asp Arg Thr Asn
                485                 490                 495
Thr Ile Ser Ser Asp Ser Ile Thr Gln Ile Pro Leu Val Lys Ser Phe
                500                 505                 510
Asn Leu Asn Ser Gly Thr Ser Val Val Ser Gly Pro Gly Phe Thr Gly
            515                 520                 525
Gly Asp Ile Ile Arg Thr Asn Val Asn Gly Ser Val Leu Ser Met Gly
    530                 535                 540
Leu Asn Phe Asn Asn Thr Ser Leu Gln Arg Tyr Arg Val Arg Val Arg
545                 550                 555                 560
Tyr Ala Ala Ser Gln Thr Met Val Leu Arg Val Thr Val Gly Gly Ser
                565                 570                 575
Thr Thr Phe Asp Gln Gly Phe Pro Ser Thr Met Ser Ala Asn Glu Ser
            580                 585                 590
Leu Thr Ser Gln Ser Phe Arg Phe Ala Glu Phe Pro Val Gly Ile Ser
        595                 600                 605
Ala Ser Gly Ser Gln Thr Ala Gly Ile Ser Ile Ser Asn Asn Ala Gly
    610                 615                 620
Arg Gln Thr Phe His Phe Asp Lys Ile Glu Phe Ile Pro Ile Thr Ala
625                 630                 635                 640
Thr
```